United States Patent [19]

Podell et al.

[11] Patent Number: 4,548,844

[45] Date of Patent: Oct. 22, 1985

[54] FLEXIBLE COATED ARTICLE AND METHOD OF MAKING SAME

[75] Inventors: Howard I. Podell, 28 Beachfront La., New Rochelle, N.Y. 10805; Albert Goldstein, Tinton Falls, N.J.

[73] Assignee: Howard I. Podell, New Rochelle, N.Y.

[21] Appl. No.: 700,057

[22] Filed: Feb. 11, 1985

Related U.S. Application Data

[63] Continuation of Ser. No. 445,760, Nov. 30, 1982, abandoned, which is a continuation-in-part of Ser. No. 216,889, Dec. 16, 1980, Pat. No. 4,482,577.

[30] Foreign Application Priority Data

Sep. 3, 1982 [GB] United Kingdom ................. 8225200

[51] Int. Cl.$^4$ ........................ A61D 19/04; B05D 3/10
[52] U.S. Cl. .......................................... 428/35; 2/168;
427/2; 427/307; 427/322; 427/341; 427/387;
427/393.5; 427/412.1; 427/430.1; 428/492;
428/520
[58] Field of Search ................ 427/2, 341, 430.1, 322,
427/307, 393.5, 387, 412.1; 428/35, 520, 492;
2/168

[56] References Cited

U.S. PATENT DOCUMENTS

| | | | |
|---|---|---|---|
| 3,411,982 | 11/1968 | Kavalir et al. | 428/493 |
| 3,503,942 | 3/1970 | Seiderman | 427/2 |
| 3,515,579 | 6/1970 | Shepherd et al. | 427/421 |
| 3,695,921 | 10/1972 | Shepherd et al. | 427/2 |
| 3,813,695 | 6/1974 | Podell et al. | 2/168 |
| 3,849,185 | 11/1974 | Shepherd et al. | 427/2 |
| 3,852,826 | 12/1974 | Schindler | 2/168 |
| 3,856,561 | 12/1974 | Esemplare et al. | 7/139 |
| 3,933,407 | 1/1976 | Tu | 427/393.5 |
| 4,082,862 | 4/1978 | Esemplare et al. | 427/333 |
| 4,143,423 | 3/1979 | Sternlieb | 427/2 |
| 4,337,111 | 6/1982 | Kaufman | 427/412.1 |

FOREIGN PATENT DOCUMENTS

| | | | |
|---|---|---|---|
| 1434453 | 3/1965 | France. | |
| 2193710 | 2/1974 | France. | |
| 2293486 | 12/1975 | France. | |
| 208084 | 7/1956 | United Kingdom | 427/307 |
| 1268637 | 3/1972 | United Kingdom. | |
| 1496345 | 12/1977 | United Kingdom. | |
| 1532216 | 11/1978 | United Kingdom. | |

*Primary Examiner*—Norman Morgenstern
*Assistant Examiner*—Janyce A. Bell
*Attorney, Agent, or Firm*—Darby & Darby

[57] ABSTRACT

There is provided a flexible rubber or article having a coating of a hydrophilic hydrogel polymer. The coating is applied to at least one surface of the article prior to heat vulcanization of the article and prior to curing of the polymer to impart lubricant and moisture transmission properties after vulcanization and curing thereof. A solution of a trivalent cationic salt may be applied to the article prior to or simultaneously with the application of the polymer so as to provide for improved adhesion of the polymer to the article after curing. A powderless solution of an emulsion or a surfactant is applied to the article after curing to reduce the surface tack of both the surface of the article which has been coated by the polymer and the surface opposite such polymer-coated surface.

21 Claims, 2 Drawing Figures

U.S. Patent    Oct. 22, 1985    4,548,844

FLEXIBLE COATED ARTICLE AND METHOD OF MAKING SAME

This application is a continuation of copending application Ser. No. 445760 filed Nov. 30, 1982, now abandoned, which is a continuation-in-part of co-pending application Ser. No. 216,889 filed on Dec. 16, 1980 now U.S. Pat. No. 4,482,577 by the same inventors.

BACKGROUND OF THE INVENTION

1. Field of the Invention

This invention pertains to flexible articles such as surgeon's glove and similar articles, and to improved methods of producing such articles. More specifically, the invention relates to surgeon's gloves having moisture absorbent and lubricant means.

2. Description of the State of the Art

U.S. Pat. No. 3,813,695 of Podell et al describes a surgeon's glove in which the need for lubricating powders for ease of donning is eliminated by providing a hydrophilic coating of a hydrogel plastic as the interior surface of the glove. This patent U.S. Pat. No. 3,813,695 recites the said coating as being formed of a polymerized coating of hydrogel resin that is applied to the interior surface of a conventional flexible vulcanized rubber glove. A solution of silicone resins may be applied to the polymerized coating so as to increase the lubricity of the coating.

Co-pending application Ser. No. 408,889 filed by the applicants on Aug. 13, 1982, of which this is a continuation-in-part, and co-pending application Ser. No. 408,094 filed by applicant Goldstein on Aug. 13, 1982, which is a continuation-in-part of abandoned application Ser. No. 216,890 filed on Dec. 16, 1980, describe a hydrogel coating polymer and a process for applying the polymer to the inner surface of a vulcanized surgeon's glove. These applications and U.S. Pat. No. 3,813,695 are hereby incorporated by reference in this application.

Other U.S. patents describe the coating of other flexible rubber articles, such as catheter and a bathing cap with such hydrogel polymers by causing them to be dipped in a casting resin with the polymer being subsequently polymerized onto the rubber substrate.

Other patents relating to this art include U.S. Pat. Nos. 3,326,742; 3,607,473; 3,966,530; 3,940,533; 3,585,103; 3,901,755; 3,966,530; 3,745,042; 3,925,138; 3,930,076; 4,125,477; 4,024,317; 3,326,742; and 4,110,495; and U.K. Pat. Nos. 1,028,446; and 859,297.

Co-pending UK provisional application, No. 8225200 filed on Sept. 3, 1982, and co-pending U.S. application Ser. No. 445,436, now U.S. Pat. No. 4,499,154, entitled "Dipped Rubber Article", filed on the date of this application by the applicants jointly with other inventors includes disclosures of the instant invention. In turn, the instant application includes disclosures of said applications as an embodiment of the instant invention under production conditions. The other applications do not claim the instant invention, and the instant application does not claim the invention of the other applications. The said U.S. application is hereby incorporated by reference in this application.

None of the cited patents or patent applications suggest the instant invention as described and claimed herein.

SUMMARY OF THE INVENTION

The invention is a surgeon's glove with improved vapor transmission properties which is formed with a coating of hydrophilic hydrogel polymer on the internal surface of said glove such that perspiration, which is absorbed by the hydrogel polymer, evaporates and is transmitted through the glove wall in substantially increased amounts as compared to the transmission of vapor through the wall of a conventional surgical glove which has not been processed in accordance with the process of this invention. The effect of this increased transmission of water vapor molecules through the glove wall is a marked increase in the cooling effect of the glove on the hand of the wearer.

An important improvement in the use of our invention lies in the increased comfort and coolness experienced by the wearer of our surgeons glove. In use, a surgeon's glove may be worn for a period of hours. During this time, the conventional glove acts as an insulator of body heat about the hand as well as a barrier to the flow of moisture vapor.

By means of the structure of our glove, accomplished by the unique technique of fabrication of this invention, wearers of the surgeons glove of our invention report that they actually feel considerable coolness about their glove-covered hands, which provides a feeling of comfort, as contrasted with their experience when wearing conventional gloves of this type.

We have determined by tests that the structure of the vulcanized latex and hydrogel polymer of the finished glove provides a substantial increase in the amount of moisture vapor transmitted through the finished glove, ranging from 25% and more. This increased flow of moisture vapor provides for a proportionately greater amount of evaporation of perspiration from the skin of the glove-covered hand which results in the increased coolness observed by the users of the glove. The evaporation of perspiration under the glove and the accompanying cooling effect are limited by the amount of evaporated moisture vapor that can pass through the wall of the glove.

It is an important feature of this invention, that the hydrogel polymer be applied in an aqueous or organic solvent solution to the latex rubber of the glove, prior to the final vulcanization of the latex rubber of the glove. The final vulcanization of the rubber occurs simultaneously with the curing of the hydrogel polymer. This treatment substantially increases the ability of the cured rubber-polymer composite to transmit water vapor from the water-absorbent hydrogel coating of the inner glove surface through the glove wall and to the ambient atmosphere.

The process of our invention results in excellent adhesion of the hydrogel coating on the inner glove surface to the rubber substrate, even when the rubber substrate is stretched to double or triple its length.

An additional advantage of our process of producing the glove of this invention lies in the fact that the external outer surface of the glove is rendered tack-free without the requirement of being subsequently washed in a slurry of powder as in the processing of conventional rubber surgical gloves. Our process provides for washing of the finished glove in a surfactant or an emulsion such as an aqueous silicone solution, and drying the washed glove in a heated oven, prior to a final rinse in water. As a result, the outer glove surface is rendered tack-free by the reaction of the silicone wash to the external outer glove surface opposite to the glove surface to which the hydrogel coating was applied in processing. It is an important advantage of our invention that the outer glove surface has been rendered tack-free without the use of any powder because such powder falling off the outer glove surface, while the glove is in use, could contaminate the tissues of a patient being surgically operated upon by a wearer of the glove. With a conventional surgeon's glove, washing the external (and internal) surface of the finished glove in a non-powder bath only, such as the silicone solution of the instant process, does not prevent the glove surfaces from becoming relatively tacky and likely to adhere to other tacky portions of such surfaces, after the surfaces have been dried. Such tackiness is undesirable in a packaged glove, since adjoining tacky glove surfaces of a packaged folded glove will adhere to each other and interfere with the donning routine after the glove is removed from its package.

An additional undesirable disadvantage of even a slightly tacky outer glove surface experienced when the glove is worn, is the resulting uncomfortable sensation felt by the fingers of the wearer when the abutting outer glove surfaces of the finger areas tend to stick together.

The process of our invention treats directly the inner glove surface (which is outermost upon the glove-forming mandrel during the processing operation) but it is this treatment which results in some of the coating material penetrating the rubber latex film through the glove wall so that the outer, otherwise not directly treated glove surface, is rendered tack-free by the direct treatment of the inner glove surface.

The process of our invention results in the improvement of the finished product by furnishing increased adhesion of the coating of the hydrogel polymer to the rubber substrate. An improved quality of adhesion of the hydrogel polymer in the finished product has been found to be due to the use of aluminum cation or other cation of a valence of three or greater in a priming solution applied prior to coating of the article in the hydrogel polymer coating solution, or the addition of aluminum cation or other such cation of a valence of three or greater to the polymer coating solution itself.

The most plausible hypothesis for the increased effectiveness of trivalent metal ions in the priming solution as compared with the lack of such effectiveness of monovalent and divalent metal ions, and particularly such trivalent ions in an acidic solution, is that such ions form a multiplicity of linkages with, on the one hand, the hydroxyl and carboxyl groups of the hydrogel polymer, and on the other hand, various non-rubber constituents in the rubber latex film—in particular with proteinaceous substances. A single ion which is linked both to the hydrogel macromolecule and to a molecule embedded in the rubber will clearly function as a bonding agent. According to this hypothesis, the efficacy of trivalent metal ions arises from the number of bonds which they can form. On this basis, other things being equal, metal ions of a valence of four or five would be even more effective. However the higher valence ions above a valence of three are subject to extensive hydrolysis and therefore function for the most part presumably as ions of lower valency.

It is well known that both aluminum and ferric ion have a strong affinity for oxygen, especially in respect to the formation of chelate complexes with carboxyl, carbonyl and hydroxyl groups. It is quite likely that strong chelates form between these trivalent metal ions and a hydrogel polymer which contain both carboxyl and hydroxyl groups. Aluminum has a strong affinity for nitrogen, with the probable formation of chelates. This may explain the mechanism whereby the aluminum ions become firmly bonded to the proteinaceous and other nitrogen-containing non-rubber constituents of the latex film. Since ferric ions do not show such a high affinity for nitrogen, the bonding to rubber of the ferric ions may occur only through the formation of chelates and other complexes with oxygen-containing groups in the non-rubber constituents.

Regardless of the actual mechanism involved, we have found that a marked improved adhesion of the hydrogel coating to the rubber substrate of the finished product results from use of the process of the invention in which aluminum or ferric ions in an acidic solution are supplied to the rubber substrate prior to dipping the substrate into the hydrogel or when such ions are in the actual polymer coating solution itself.

BRIEF DESCRIPTION OF THE DRAWINGS

The objects and features of the invention may be understood with reference to the following detailed description of an illustrative embodiment of the invention, taken together with the accompanying drawings in which.

DESCRIPTION OF THE PREFERRED EMBODIMENT

Figure 1:
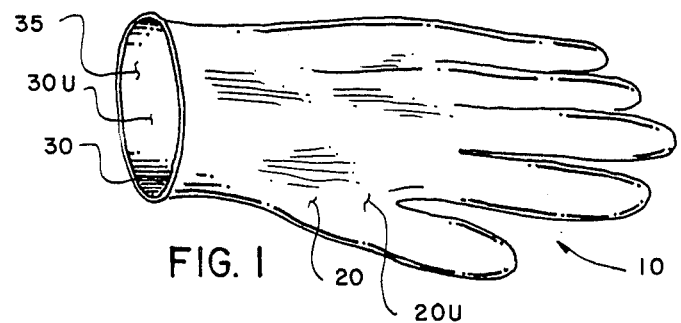
FIG. 1 is a perspective view of the invention.

FIG. 1 illustrates the invention in the form of a finished latex rubber surgeon's glove 10. The inner surface 30 of the glove 10 has been coated with a hydrogel polymer, during fabrication of the glove and prior to the final vulcanization of the rubber of the glove. The hydrogel coating becomes bound to the inner surface 30 so as to form an inner surface with excellent slip properties that provide for ease of donning the glove by the hand of a wearer and eliminate the requirement for conventional lubricating powders. The glove exhibits hypoallergenic properties in that wearers of the glove who are allergically responsive to conventional latex rubber gloves have reported a complete lack of any allergenic response, when wearing the glove of the invention. The hydrogel coating is of a hydrophilic nature and absorbs perspiration of the skin. Wearers of the gloves of the invention report greater comfort and coolness to their hands as compared with the wear of conventional powdered gloves.

The following description is of each of several processes employed in the fabrication of the invention. Solutions will be defined as by weight, temperatures given in degrees Celsius(°C.), and "ambient temperature" taken to be in the range of 17° to 20° C.

The surgical or surgeon's glove 10 of the invention, is customarily initially fabricated by dipping processes well known in the art. For purposes of description in this application, the outer surface 20 of the glove 10 is defined as the glove surface which becomes the external glove surface 20U in the position of actual use, when worn, with the inner glove surface 30 defined as the surface 30U adjacent to the skin of the wearer, in use. It should be recognised that in the initial steps of fabrication of the invention, these glove surfaces are reversed. In normal fabrication, a surgical glove is formed about a porcelain mandrel 50 of the shape of a hand, with the outer surface 20 adjacent the glove mandrel, and the inner surface 30 externally exposed.

Figure 2:
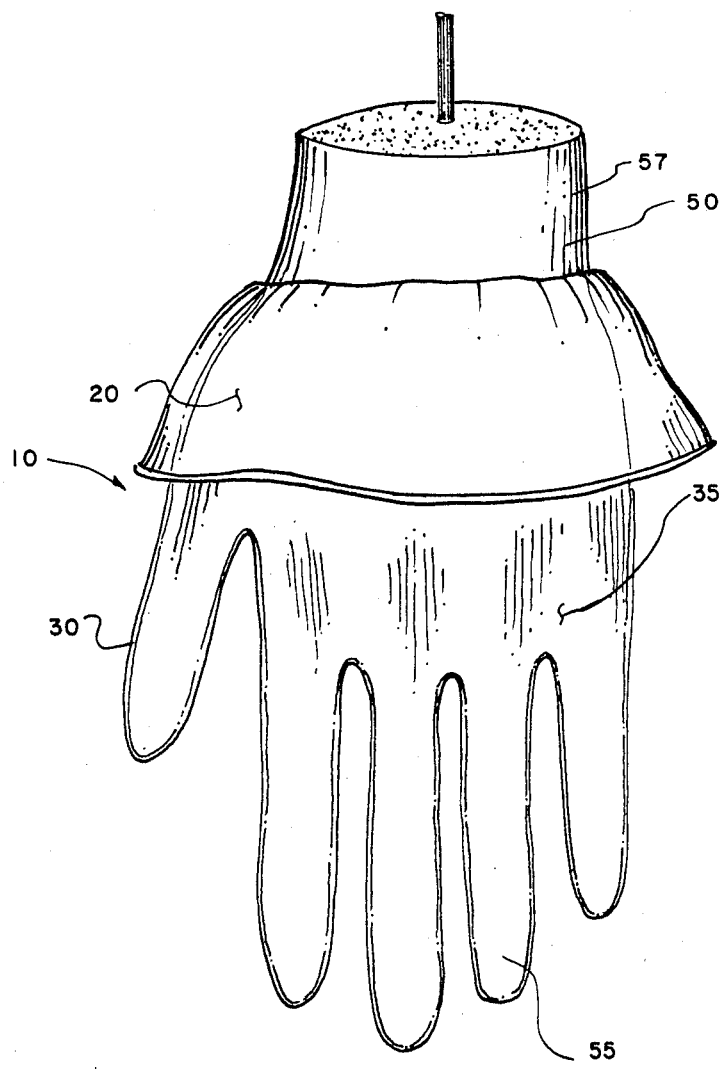
FIG. 2 is a perspective view of the glove of the invention being stripped from a glove mandrel during processing.

This mandrel is initially dipped in a coagulant solution, dried and then dipped in a liquid rubber latex. The glove surface which forms adjacent to the mandrel, during such processing is the outer glove surface 20, with the inner glove surface 30 being externally exposed on the glove mandrel. The rubber-coated mandrel is then dipped in a leach solution to dissolve out and wash away the coagulant salts and then heated at a temperature to partially vulcanize the rubber for a period of time. In the normal removal of the vulcanized glove from the mandrel after this heating step, the glove is manually pulled off the mandrel by gripping the uppermost cuff portion of the glove, and pulling it towards the finger section of the glove over the glove, causing reversal of the external and internal glove surfaces into the position of final use, as shown in FIG. 2.

Prior to our invention, removal of the gloves from the mandrel was accompanied by washihng the glove mandrel in a lubricating solution, such as a powder slurry to prevent adhesion of the otherwise tacky inner and outer glove surfaces. Regardless of the lubricating solution employed, it was necessary to apply powder such as talc or a starch product to the glove surfaces prior to the final rinsing of this lubricant solution and to the gloves becoming dry.

In one embodiment of the process of our invention, the rubber-coated glove mandrel, is dipped into one or more priming solutions after the above leach step, and subsequently dipped into one or more rinse and/or neutralization solutions and finally dipped into a solution of the hydrogel polymer prior to entering the heating oven for drying and vulcanization of the rubber latex and for curing of the hydrogel polymer. During these dipping operations, the mandrel may be vertically positioned with the finger sections 55 pointed downwards and with the uppermost section 57 of the mandrel maintained above the liquid level in each dipping tank.

During the heating operation, the hydrogel polymer adheres to and permeates the rubber of the glove, to form a coating on the exposed inner glove surface of hydrogel polymer and to affect the structure of the rubber glove wall and outer glove surface which is adjacent the glove mandrel.

After removal from the heating oven, the glove may be washed with a dilute soap solution or with water prior to and during the stripping operation from the mandrel. A subsequent aftertreatment results in the elimination of tack from the glove outer surface 20, and this after-treatment may include a wash in a surfactant mixture that simultaneously improves the slipperiness of the inner glove surface 30 to the damp skin of a user.

In all of the following Examples A–D, the following conventional processing steps are initially performed and will be identified hereinafter as "STAGE I":

STAGE I

Each glove mandrel is dipped in customary fashion in a coagulating solution such as that of a calcium salt. In customary fashion the coagulent is dried upon the mandrel surface by application of heat, or circulation of heated air. In customary fashion, the glove mandrel is now dipped in a conventional solution of latex rubber, after which the mandrel is heated for a few minutes to dry the latex rubber upon the form. The coated mandrel is now dipped in a leach tank of water preferably heated to a temperature above seventy degrees (70°) Celsius for several minutes.

EXAMPLE A

After step I, the coated mandrel is briefly rinsed in running water, and then dipped into a solution of dilute sulfuric acid, ranging in concentration from 2% to 5%. The acid is maintained at an ambient temperature of about twenty degrees Celsius. Acid solutions of up to 20% may be employed, but such higher strengths may cause discoloration and damage to the unvulcanised rubber. The mandrel is held in the 2% acid solution for a period of 15 to 30 seconds. After removal from the acid solution, the mandrel is quickly dipped in a rinse bath of water or of a dilute alkaline solution such as of ammonia, or ammonium hydroxide, and then dipped for a period ranging from 30 to 45 seconds in an aqueous solution of 4% aluminum sulfate held at a temperature ranging from 60° C. to 80° C. The mandrel is then rinsed with hot running water at 70° C. and dipped in a polymer solution at ambient temperature for a period of 20 to 40 seconds.

The polymer solution is a 1.5% aqueous solution of a custom made hydrogel polymer (Our custom-made #MP-83, described hereinafter) to which 20 phr (parts per hundred parts polymer resin) of Cymel brand #373, a brand of hydroxymethylated melamine and 2 phr of para-toluenesulfonic acid monohydrate (PTSA) have been added. The polymer solution is brought to a pH of 6.5–7.0 by adjusting with ammonia as required.

The treated mandrel is now heated in a circulating hot air oven for approximately 30 minutes. The oven temperature is intially at 80° C.–90° C. but rises to reach a temperature of 105° C. for at least ten minutes of this heat cure cycle. The mandrel containing the vulcanized glove is removed from the oven and dipped into a bath of water, which may contain a few drops of a soap solution such as Pluronic brand L-51. After this brief rinse, the glove is stripped from the mandrel, preferably under running water, or a rinse of running water and surfactant solution and then rinsed in the surfactant solution. The surfactant solution is a 1% aqueous dispersion of SAG-10 brand of silicone emulsion (0.1% solids). After rinsing in the surfactant solution, the finished gloves are air-dried in a hot oven at a temperature of 105° C. for a period of thirty minutes.

The dried gloves exhibit excellent slip when donned on relatively dry hands and require no additional lubricant or powder for the lubrication of the inner glove surface. The outer surface of the glove is tack-free and the finger sections may be manually squeezed together, with the finger sections separating completely from each other, without adhesion, after release of clamping pressure.

To determine the extent of the water absorption properties of the hydrogel coating of the inner surface, a treated glove is immersed for a minute in an aqueous dye such as a 1% solution of methyl violet, and then rinsed in clear water to wash off unabsorbed dye excess. The density of the dye color remaining after drying of the glove is a measure of the water absorbtion of the coating and the relative thickness of the coating.

EXAMPLE B

The procedure is similar to Example A, except that the separate dip in dilute acid solution and subsequent rinse is omitted, and the parameters of the priming dip in aluminum sulfate solution were changed as follows:

After removal from a leach rinse, and a fresh water rinse, the mandrel is dipped for a period of 30 to 80 seconds into a 6% aqueous solution of aluminum sulfate (12.5% of alum hydrate) held at 70° C. with the pH of the solution adjusted to a pH of 2.0 by addition of sulfuric acid. After removal from the dip tank, the mandrel is washed with water at 70° C. to rinse off the excess aluminum sulfate and restore mandrel temperature. The mandrel is then dipped into the hydrogel solution as stated in Example A. The concentration of the hydrogel solution may be varied from 3/4% to 2% to obtain desired thickness of coating, with the more concentrated solution resulting in thicker and more slippy coatings.

The finished glove is of equal quality to that produced in Example A. However a separate acid dip step has been eliminated.

EXAMPLE C

The process is similar to Example B except that the dipping operation in the aluminum sulfate solution and the subsequent rinse has been eliminated, by the addition of aluminum sulfate into the polymer dipping solution, to result in a one dip process.

After removal from the Leach tank, and a rinse with water, the rubber latex coated mandrel is immediately dipped into an aqueous solution at ambient temperature made up as follows:

28.4 grams alum hydrate (including 14 parts of water per molecule of aluminum sulfate)
1136 grams of 20% aqueous solution of Polymer #MP83
80.0 grams Cymel Brand #373 (Amer Cyanamid)
2.14 grams of 85% Phosphoric Acid
Add water to make 3400 grams
Adjust pH of solution to range of 5.5–6.5 using ammonium hydroxide.

This solution is a 6⅜% (real) solution of the polymer, with the ratio of the weight of aluminum sulfate (dehydrated) to polymer being of the order of 1 to 8.4.

In the preparation of this dipping solution, the aluminum sulfate is initially dissolved in a quantity of water and then brought to a pH of 5.5. It is then gradually mixed with a solution containing the remainder of the water and the polymer, with vigorous stirring.

The results achieved with the one coating dip process of Example C exhibited hydrogel coatings on the inner glove surface of desirable slip and adhesion characteristics. The treated gloves were readily donned, without the need for any lubricating powders, when applied to the dry hands of the wearer. The coating process of Example C does not require any additional dipping or priming operations aside from the single dip into the polymer-aluminum sulfate solution. After the vulcanization of the gloves, and their removal from the mandrel, the gloves are washed in an aqueous silicone solution of 0.5% DC365 medical grade silicone (Dow Corning) and then dried by heat at 105° C.

This one dip operation of Example C may be employed substituting other trivalent cation salt solutions for the aluminum sulfate, or solutions of cation salts where the valence of the cation is greater than three. Indeed similar results were achieved substituting ferric sulfate for the aluminum sulfate on a mol for mol basis. The ferric salt is unsatisfactory only in that it stains the finished glove. Additional tests indicated that the salt could be formed using any of several anions which resulted in a soluble salt in solvent of the polymer solution. Thus aluminum nitrate and aluminum chloride were found to be satisfactory equivalents of the aluminum sulfate when the polymer is held in an aqueous solution. Satisfactory coatings resulted when the polymer was dissolved in an ethanol solution and the aluminum cation was added in the form of soluble aluminum nitrate.

The process of Example C was found to provide little or no coating results when other salts, formed of cations of lesser valence than three, (instead of those of trivalent cations), were added to the polymer solution instead of a salt of a trivalent cation. Where the substituted salt was that of a cation in the form of a bivalent metal ion such as that of calcium, zinc, or the ferrous ion, the finished glove exhibited little slip on the inner surface and could not be satisfactorily donned by the dry hand of a user.

EXAMPLE D

The process of Example D represents an improvement over the processes of these applicants for production of a hydrogel coated surgeon's glove and is disclosed in UK provisional patent application No. 8225200 and U.S. application Ser. No. 445,436, now U.S. Pat. No. 4,499,154, directed to a Dipped Rubber Article and filed simultaneously with the instant application. The improved process of Example D was developed jointly by these and other inventors. The improved process of Example D is disclosed herewith solely as an example of a preferred mode of making the surgical glove of the invention under production conditions. The applicants do not claim as their invention, in the instant application, the improved process nor product of Example D, to the extent that it differs from the processes and products invented by the applicants and exemplified by Examples A, B, and C of this application. The glove produced by the improved process of Example D exhibits the desirable properties of the gloves of the invention of the applicant, but in addition exhibits additional desirable properties of increased slip of the coated surface when the glove is donned by a damp or wet hand, and other improved features as contrasted with the surgical gloves produced by examples A, B and C.

After completion of Step I, the rubber coated mandrel is dipped for 15–30 seconds into a solution of 1–2% Sulfuric acid at a temperature of 40° C. The mandrel is then rinsed with water and dipped for a similar period into a neutralizing bath of dilute caustic preferably held at a pH of 9–10. The mandrel may then be dipped into one or more wash tanks of water heated to 40° C. and finally dipped for about 15 seconds into a coating solution of a polymer in ethanol. The polymer dip solution may be at a temperature ranging from ambient to 40° C.

The polymer coating solution of Example D is preferably a terpolymer of 2-hydroxyethyl methacrylate (HEMA), methacrylic acid (MAA) and 2-ethylhexyl acrylate (EHA) diluted to a concentration of 4% in concentrated ethanol, with the monomers initially present in the mol ratio of 25:5:6 respectively. Ten percent (by weight) of Cymel 370 as a cross-linking agent and one percent of Para-toluenesulfonic acid (Cycat brand #4040) as a catalyst, is added to the coating solution.

After being dipped in the hydrogel polymer solution, the mandrel is heated in an oven for 30 minutes with temperatures rising to 105° C.

Subsequently, the gloves of Example D are stripped from the mandrel, as shown in FIG. 2, and immersed for 15 minutes in a solution of Surfactant (#D). Surfactant solution #D is an aqueous dispersion of 0.05% of 35% Silicone medical grade emulsion DC365 (Dow Corning brand) and 0.5% Cetylpyridinium chloride. After draining, the gloves are heated and dried in an oven for 30 minutes at 70° C.

Gloves made in accordance with Example D incorporate all of the desirable characteristics of the invention. The Example D gloves are of hypoallergenic quality, and exhibit the increased moisture vapor transmission characteristics of the invention. The outer surface of the glove is tack-free. The inner coated surface is hydrophilic, has a high degree of slip and is readily donned on a dry hand.

One of the additional improvements of the gloves produced by the process of Example D over the gloves of the this instant invention of the applicants lies in the achievement of the high degree of slip that the coated hydrogel surface exhibits against damp or wet skin of a wearer's hand, while being donned.

Water Vapor Transmissibility

The following are the results of tests made of the rate of moisture transmission through the wall of the glove across a gradient of 100% relative humidity at an ambient temperature of 25° C. over a 72 hour period of time.

| TEST SAMPLE | PROCESS EXAMPLE | WATER VAPOR TRANSMITTED $gm/m^2/mm/24$ hr |
|---|---|---|
| I | D | 7.86 |
| II | | 7.73 |
| III | C | 9.76 |
| IV (Control) | Prior Art | 4.22 |

All test samples I–IV were produced from individual gloves, processed in the same fashion according to STAGE I. Each mandrel was dipped for the same length of time in the same latex rubber, and subsequently dipped in the leach tank.

The control sample IV was then processed in accordance with conventional procedure, going from the leach tank directly into the heating oven for final vulcanization, without any further treatment and without any process in accordance with the teaching of this application.

The test sample I was subsequently processed in a similar fashion to the process described in Example D, a process which is described in detail in co-pending U.S. application Ser. No. 445,436 now U.S. Pat. No. 4,499,154, filed by the applicants jointly with other inventors on the same date as this application, entitled "Dipped Rubber Article".

The test sample II was subsequently processed in similar fashion to the process described in Example C, except for the use of a polymer held in a solution of concentrated ethanol and with aluminum nitrate substituted for aluminum sulfate in the polymer solution. The polymer solution of test sample II was a terpolymer as described in the process of Example D.

The test sample III was subsequently processed in similar fashion to the process as described in Example C.

It is evident from these test results that there is a substantial increase of moisture vapor transmission through the wall of the gloves fabricated in accordance with the teachings of this invention ranging in magnitude from 86% to 131% increase. In other tests, made by comparing moisture vapor transmission rates using method 7032 of Fed. Test Method STD No. 406 an increase of moisture vapor transmission of 28.8% was found in gloves processed in accordance with the described invention and conventional surgical gloves. It is to be noted that an increase of over 25% of moisture vapor transmission through the glove will result in increased evaporation of perspiration on the enclosed hand of the wearer with a consequent considerable increase in cooling and in increased comfort to the hand of the wearer.

The increase of moisture vapor transmissibility in gloves of the invention occurs from the reaction of the hydrogel processing solutions with the latex rubber on the glove mandrel prior to and during the final heat vulcanization of the latex rubber.

POLYMER

Various hydrogel polymers including those described in co-pending U.S. application Ser. No. 408,094 filed on Aug. 13, 1982 may be employed as coating polymers to produce the invention.

A preferred coating polymer employed by the applicants in the processes of Examples A, B and C, identified as Custom Mix MP-83, is an aqueous solution of a copolymer of 90% 2-Hydroxyethoxy methacrylate (HEMA) and 10% acrylic acid (AcAc) that is produced as follows:

In a 12 liter flask,
Charge:
Gelvatol 20/30(Air. Prod. Co.)     43.0 g.
Polyvinylalcohol
Water at 60° C. to 70° C.     5320.0 g.
Stir to dissolve the Gelvatol; sparge in nitrogen at the rate of 0.4 liter/min. for 20 minutes.
Add: at 45° C.
Triton X305(Rohm & Haas)     86.8 g.
Dispersion Agent
Cool to 38° C. and Add:
HEMA liquid monomer     258.8 g.
AcAc liquid monomer     28.4 g.
Continue to sparge with Nitrogen @ 0.4 liter/min. for 30 min.
Add at 37° C., consecutively:
Ammonium persulfate     13.76 g.     in 40 ml. of water
Sodium Bisulfite     2.84 g.     in 20 ml. of water
Add at a temperature of 38–41° C., the following mixture over a period of 2½ hr. controlling the exotherm heat by cooling:
HEMA liquid monomer     776.0 g.
AcAc liquid monomer     86.8 g.
Then HEAT TO 60° C. for 25 min.
Heat at 60° C.–63° C. for 45 minutes and Add:
Dow Corning Anti-Foam     3.0 ml.
Agent #544
Distill away, at 100° C., 590 ml. of water,
Cool to 70° C.
Add appr. 110 ml. of 28% Ammonium Hydroxide to reach 7.25 pH appr., then
Cool to room temperature.

The polymer solution after the above processing for a typical run tested out to 21.05% solids with a viscosity of 296 cps as measured on a Brookfield RVT (spindle #2 at 100 rpm).

It should be noted that conventional methods of preparation of a solution of a copolymer containing over 70% HEMA required the use of an organic solvent since some of the HEMA would precipitate out of an aqueous solution, at such concentrations. However the step of adding the ammonium hydroxide at an elevated temperature of about 70° C. which is lower than the distillation temperature and substantially above the ambient temperature serves to maintain the HEMA in solution at the concentration of 90% HEMA to 10% AcAc, with the copolymer in a 21% aqueous solution.

In all polymer mixes, prepared for dipping, we have used a curing or cross-linking agent such as Cymel brand 373 and an acid catalyst such as para-toluenesulfonic acid, or phosphoric acid, or an ammonium salt that decomposes to an acid under heat such as ammonium phosphate.

OTHER PRODUCTS

We have coated other products in similar fashion such as finished rubber catheters, synthetic plastic threads and fabrics such as those formed of polyester, nylon and acrylic materials and have bonded hydrophilic water absorbing hydrogel coatings to such materials with improved adhesion of such coatings as compared to coatings obtained by methods of the prior art. It will be realized that such other coatings may be of greater or lesser thicknesses than those desired for surgical gloves. The variation of coating thickness is most readily obtained by variation of concentration of the polymer solution, although a variance in the dip time, temperatures and concentrations of other elements of the process may be employed for optimum results. The priming and coating operations described in Examples A,B, and C may be employed in dipping fully vulcanized or fully cured materials.

Where the practice of the invention has been described in terms of a copolymer of hydroxyethoxy methacrylate and acrylic acid, it will be understood by those skilled in the art that other hydrophilic polymers may be used as equivalents to provide the features of the invention.

Thus methacrylic acid may be used as an alternative for acrylic acid, and 2 hydroxyethoxy ethyl acrylate or methacrylate, or a hydroxyalkyl acrylate or methacrylate may be employed instead of the 2-hydroxyethoxy methacrylate, where the hydroxyethoxy alkyl group may be defined as hydroxy ethyl, hydroxy propyl, or 2-3di-hydroxy propyl.

Other hydrophilic polymers that may be employed instead of the described polymer include those which are copolymers containing N-vinyl-2-pyrrolidinone, glycerl methacrylate or acrylate, or graft copolymers of polyvinyl alcohol, or partially hydrolyzed polyacrylonitrile.

It is thought that persons skilled in the art to which this invention pertains will be able to obtain a clear understanding of the invention after considering the foregoing description in connection with the accompanying drawing. Therefore, a more lengthy description is deemed unnecessary.

It is understood that various changes in the arrangement of the elements of this invention may be resorted to in actual practice, if desired, to achieve the described effects and such changes that are indicated from the above description of the invention are considered to be part of the invention of the applicants.

Having thus described our invention, what we claim as new and desire to secure by Letters Patent of the United States is:

1. A flexible rubber article of substantially tubular shape for use against human skin or tissue, said article having been treated by the application of an adherent coating of a hydrogel polymer to an outer surface of said article, said hydrogel coating imparting on said outer surface moisture absorbent properties manifested by a feeling of increased coolness on the part of a wearer of said article, and providing said surface with a compatible interface against human skin or tissue during use of said article, said article having been primed with a dilute acid and coated with a solution of said hydrogel polymer prior to final vulcanization of the rubber of said article.

2. A flexible rubber article for use in contact with human or animal skin or tissue, said article having been treated by priming with a dilute acid followed by the application of an adherent coating of a hydrogel polymer solution to one surface of said article prior to final vulcanization of said article so as to form an external surface after curing of said coating, said cured external surface imparting moisture absorbent properties to said article surface and providing said article surface with a coating that is compatible with said skin or tissue, said article having been also treated by dipping in a dilute solution of a soluble salt of an at least trivalent metal ion, prior to curing of the hydrogel coating so as to increase the adherence of said polymer coating to said article after curing of the polymer coating.

3. An article as recited in claim 2, in which said article has been dipped in a dilute acid solution prior to being dipped in said salt solution.

4. An article as recited in claim 2, in which said article has been dipped in said salt solution prior to dipping in a solution of said polymer.

5. An article according to claim 2, in which an acid is incorporated into said salt solution.

6. An article according to claim 5, in which said salt solution is incorporated into the polymer solution.

7. An article according to claim 2, wherein said polymer incorporates a substantial amount of 2-hydroxyethoxy methacrylate and acrylic acid.

8. The article of claim 1, in the form of a sheet.

9. The article of claim 1 in the form of a glove.

10. The article of claim 2 in the form of a condom.

11. The article of claim 2 in the form of a catheter or urether.

12. The article of claim 1 in the form of a tube.

13. An article according to claim 1, said article being a surgical glove, said hydrogel coating lying on the inner surface of said article, wherein both said inner surface and the outer surface opposite said inner surface have been rendered substantially tack-free, without contact with a powder material, by the application of a liquid powderless surfactant to said glove surfaces subsequent to vulcanization of said rubber and curing of said polymer.

14. An article according to claim 13, wherein said surfactant is in the form of a dilute aqueous solution of a silicone surfactant.

15. An article according to claim 9, wherein said hydrogel polymer is applied in the form of an aqueous solution containing 0.5–10% of said polymer by weight.

16. A process for producing a rubber article, said article comprising an adherent coating of a hydrophilic hydrogel polymer applied to at least one surface thereof, said article having both lubricant properties and vapor transmission properties the latter being manifested by a feeling of coolness experienced by a wearer of said article, said process comprising:
    (a) priming a mold which has previously been coated by a rubber latex by dipping it into an aqueous solution of dilute acid;

(b) dipping said primed rubber coated mold into a solution of a hydrophilic polymer so that said polymer coats said rubber prior to full vulcanization of said rubber, (c) curing said polymer and vulcanizing the thus formed article by application of heat for a period of time sufficient to cure said polymer and vulcanize said rubber so that said polymer adheres to said rubber.

17. The process of claim 16 wherein said polymer solution contains 2-hydroxyethoxymethacrylate, acrylic acid, a curing agent, and a compound that maintains the solution in an acidic condition under heating.

18. The process of claim 16 wherein a solution of a cationic salt of a valence of at least three is applied to the article prior to application of said polymer, thereby increasing the adherence of said polymer to said rubber upon subsequent heating.

19. The process of claim 16, wherein a solution of a cationic salt of a valence of at least three is incorporated into said polymer solution, so as to increase the adherence of said polymer to said rubber upon subsequent heating.

20. The process of claim 18, wherein the cation of said salt is aluminum ion.

21. The process of claim 19, wherein the cation of said salt is aluminum ion.

* * * * *